United States Patent [19]
Hansen et al.

[11] Patent Number: 5,612,325
[45] Date of Patent: Mar. 18, 1997

[54] VITAMIN D ANALOGUES HAVING A HALOGEN-OR AZIDO- SUBSTITUTED SIDE CHAIN

[75] Inventors: Kai Hansen, Herlev; Henrik Pedersen, Bagsværd, both of Denmark

[73] Assignee: Leo Pharmaceutical Products Ltd. A/S (Løvens Kemiske Fabrik Produktionsaktieselskab), Ballerup, Denmark

[21] Appl. No.: 367,206

[22] PCT Filed: Sep. 23, 1993

[86] PCT No.: PCT/DK95/00305

§ 371 Date: Jan. 3, 1995

§ 102(e) Date: Jan. 3, 1995

[87] PCT Pub. No.: WO94/07851

PCT Pub. Date: Apr. 14, 1994

[30] Foreign Application Priority Data

Sep. 25, 1992 [GB] United Kingdom .................. 9220272

[51] Int. Cl.$^6$ .......................... A61K 31/59; C07C 401/00
[52] U.S. Cl. ............................ 514/167; 552/653
[58] Field of Search ............................ 552/653; 514/167

[56] References Cited

U.S. PATENT DOCUMENTS

| | | | |
|---|---|---|---|
| 4,948,789 | 8/1990 | Slatopolsky | 514/167 |
| 5,053,401 | 10/1991 | Matsumoto et al. | 514/167 |
| 5,254,538 | 10/1993 | Holick et al. | 514/167 |
| 5,378,695 | 1/1995 | Calverley et al. | 514/167 |
| 5,401,732 | 3/1995 | Calverley et al. | 514/167 |
| 5,403,832 | 4/1995 | Posner et al. | 514/167 |
| 5,403,940 | 4/1995 | Vallés et al. | 514/167 |

FOREIGN PATENT DOCUMENTS

| | | | |
|---|---|---|---|
| 9009991 | 9/1990 | WIPO | C07C 401/00 |
| 909991 | 9/1990 | WIPO | |

OTHER PUBLICATIONS

Kubodera, et al: "Synthetic Studies of Vitamin D Analogues, XI. Synthesis and Differentiation–Inducing Activity of 1alpha, 25–Dihydroxy–22–oxavitamin D3 Analogues", Chemical Parmaceutical Bull., vol. 40, No. 6, Jun. 1, 1992–pp. 1494–1499.

Brown, et al: "New Active analogues of vitamin D with low calcemic activity", Kidney International, vol. 38, No. 29, 1990, pp. S–22–S–27.

*Primary Examiner*—Kimberly J. Prior
*Attorney, Agent, or Firm*—Cushman Darby & Cushman IP Group Pillsbury, Madison & Sutro LLP

[57] ABSTRACT

A compound of formula I

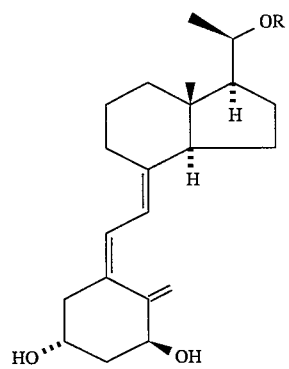

wherein R stands for a straight or branched, saturated or unsaturated alkyl group containing from 4 to 12 carbon atoms optionally substituted with a hydroxy group, and possibly containing a ring structure, and in which at least one of the carbon atoms not bearing hydroxyl group is substituted with one or more halogen atoms or an azido group; and prodrugs of I in which one or more of the hydroxy groups are masked as groups which can be reconverted to hydroxy groups in vivo, in pure form or in mixtures. The compounds show antiinflammatory and immunomodulating effects as well as strong activity in inducing differentiation and inhibiting undesirable proliferation of certain cells. The compounds are prepared by oxidizing 1(S),3(R)-bis-(tert-butyldimethylsilyloxy)-20(S)formyl-9,10-seco-pregna-5(E),7(E),10(19)-triene, reducing the resulting product; alkylating the reduction product and then subjecting the alkylated product to triplet-sensitized photoisomerization.

8 Claims, No Drawings

VITAMIN D ANALOGUES HAVING A HALOGEN-OR AZIDO- SUBSTITUTED SIDE CHAIN

This application is a 371 of PCT/DK93/00305 filed Sep. 23, 1993.

This invention relates to a hitherto unknown class of compounds which shows antiinflammatory and immunomodulating effects as well as strong activity in inducing differentiation and inhibiting undesirable proliferation of certain cells, including cancer cells and skin cells, to pharmaceutical preparations containing these compounds, to dosage units of such preparations, and to their use in the treatment and prophylaxis of hyperparathyroidism, particularly secondary hyperparathyroidism associated with renal failure, of a number of disease states including diabetes mellitus, hypertension, acne, alopecia, skin ageing, imbalance in the immune system, of inflammatory diseases such as rheumatoid arthritis and asthma, of diseases characterized by abnormal cell differentiation and/or cell proliferation such as e.g. psoriasis and cancer, for prevention and/or treatment of steroid induced skin atrophy, and for promoting osteogenesis and treating osteoporosis.

The compounds of the present invention are represented by the general formula I

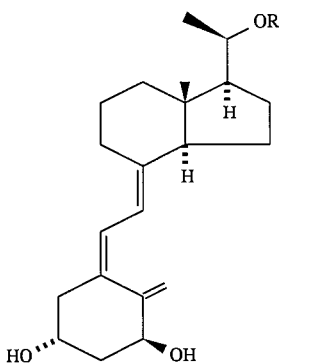

in which formula R stands for a straight or branched, saturated or unsaturated alkyl group containing from 4 to 12 carbon atoms optionally substituted with a hydroxy group, and possibly containing a ring structure, and in which at least one of the carbon atoms not bearing a hydroxyl group is substituted with one or more halogen atoms or an azido group.

Preferably R is a group of formula II

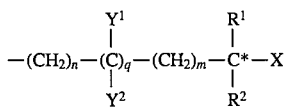

where q is 0 or 1, and n and m are independently 0 or integers running from 1 to 6; $Y^1$ and $Y^2$ are independently hydrogen, halogen or azido; $R^1$ and $R^2$ which may be the same or different, stand for hydrogen, lower alkyl, lower cycloalkyl, or, taken together with the carbon atom (starred in formula II) bearing the group X, $R^1$ and $R^2$ can form a $C_3$-$C_8$ carbocyclic ring; $R^1$ and $R^2$ may optionally be substituted with an azido group or one or more halogen atoms; X stands for hydrogen or hydroxy.

In the context of this invention, the expression "lower alkyl" indicates a straight or branched saturated or unsaturated carbon chain containing from 1 to 5 carbon atoms, and the expression "lower cyclo-alkyl" indicates a saturated or unsaturated $C_3$-$C_7$ carbocyclic ring. Halogen stands for fluorine, chlorine, bromine or iodine.

In particular, $R^1$ and $R^2$ are independently selected from the group consisting of hydrogen, methyl, ethyl, propyl, isopropyl, butyl, isobutyl, tert-butyl, sec-butyl, pentyl, fluoromethyl, difluoromethyl, trifluoromethyl, pentafluoroethyl, 2,2,2-trifluoroethyl, 2-fluoropropyl-2, 3-fluoropentyl-3, chloromethyl, trichloromethyl, 2-chloropropyl-2, 3-chloropentyl-3, bromomethyl, 2-bromopropyl-2, 3-bromopentyl-3, iodomethyl, 2-iodopropyl-2, 3-iodopentyl-3-azidomethyl, 2-azidopropyl-2, and 3-azidopentyl-3.

As can be seen from formula I and II, depending on the meanings of R, $Y^1$, $Y^2$, X, $R^1$ and $R^2$ the compounds of the invention comprise several diastereoisomeric forms. The invention covers all these diastereoisomers in pure form and also mixtures of such diastereoisomers. In addition, prodrugs of I in which one or more of the hydroxy groups are masked as groups which can be reconverted to hydroxy groups in vivo are also within the scope of the invention.

Compounds of formula I in which R is not substituted with hydroxy are another type of prodrug. These compounds are relatively inactive in vitro, but are converted to active compounds of formula I by enzymatic hydroxylation after administration to the patient.

It has been shown that 1α,25-dihydroxy-vitamin $D_3$ (1,25(OH)$_2$$D_3$) influences the effects and/or production of interleukins (Muller, K. et al, Immunol. Lett. 17, 361–366 (1988)), indicating the potential use of this compound in the treatment of diseases characterized by a dysfunction of the immune system, e.g. autoimmune diseases, AIDS, host versus graft reactions, and rejection of transplants or other conditions characterized by an abnormal interleukin-1 production, e.g. inflammatory diseases such as rheumatoid arthritis and asthma.

It has also been shown that 1,25(OH)$_2$$D_3$ is able to stimulate the differentiation of cells and inhibit excessive cell proliferation (Abe, E. et al, Proc. Natl. Acad. Sci., U.S.A. 78, 4990–4994 (1981)), and it has been suggested that this compound might be useful in the treatment of diseases characterized by abnormal cell proliferation and/or cell differentiation such as leukemia, myelofibrosis and psoriasis.

Also, the use of 1,25(OH)$_2$$D_3$, or its pro-drug 1α-OH-$D_3$, for the treatment of hypertension (Lind, L. et al, Acta Med. Scand. 222, 423–427 (1987)) and diabetes mellitus (Inomata, S. et al, Bone Mineral 1, 187–192 (1986)) has been suggested. Another indication for 1,25(OH)$_2$$D_3$ is suggested by the recent observation of an association between hereditary vitamin D resistance and alopecia: treatment with 1,25(OH)$_2$$D_3$ may promote hair growth (Editorial, Lancet, Mar. 4, 1989, p. 478). Also, the fact that topical application of 1,25(OH)$_2$$D_3$ reduces the size of sebaceous glands in the ears of male Syrian hamsters suggests that this compound might be useful for the treatment of acne (Malloy, V. L. et al., the Tricontinental Meeting for Investigative Dermatology, Washington, 1989).

However, the therapeutic possibilities in such indications of 1,25(OH)$_2$$D_3$ are severely limited by the well known potent effect of this hormone on calcium metabolism; elevated blood concentrations will rapidly give rise to hypercalcemia. Thus, this compound and its potent synthetic analogues are not completely satisfatory for use as drugs in the treatment of e.g. psoriasis, cancer or immune diseases which may require continuous administration of the drug in relatively high doses.

A number of oxa-analogues of vitamin $D_3$ are known. 1α,25-dihydroxy-20-oxa-21-norvitamin $D_3$ and 1α-hydroxy-20-oxa-21-norvitamin $D_3$ are described in N. Kubodera et al, Chem. Pharm. Bull., 34, 2286 (1986), 1α,25-dihydroxy-22-oxavitamin $D_3$ and 25-hydroxy-22-oxavitamin $D_3$ are described in E. Murayama et al, Chem. Pharm. Bull., 34, 4410 (1986), J. Abe et al, FEBS Lett. 226, 58 (1987) and European Patent Application, publication number 184 112. 1α,25-dihydroxy-23-oxavitamin $D_3$ is described in European Patent Application, publication number 78704, and a number of 22-oxa-analogues of vitamin $D_3$ are described in International Patent Application No. PCT/DK90/00037 and International Patent Application No. PCT/DK90/00036.

In vitro experiments indicate that some of these compounds may have advantages over $1,25(OH)_2D_3$. Thus 1α,25-dihydroxy-22-oxavitamin $D_3$ has only one 14th as much affinity as $1,25(OH)_2D_3$ for the chick intestinal cytosolic receptor, a weaker affinity than $1,25(OH)_2D_3$ for the receptor in a human myeloid leukemia cell line (HL-60), and a high activity as inducer of differentiation in HL-60 cells.

The usefulness of a vitamin D analogue in the above mentioned indications is dependent not only upon a favourable ratio of binding affinity to relevant receptors compared to the intestinal receptor, but also upon the fate of the compound in the organism.

It has now been found that the compounds of the present invention, with halogen at suitable positions in the side chain, show favourable selectivity with respect to receptor binding and at the same time show high bioavailability as well as metabolic stability as compared to $1,25(OH)_2D_3$.

The selectivity of the compounds is illustrated by the fact that while they have high affinities for the receptor in tumour cells (similar to or much better than that of $1,25(OH)_2D_3$) and the concentration needed to induce cell differentiation in a human monocytic tumour cell line is the same as or considerably lower than that needed of $1,25(OH)_2D_3$ to give the same effect, their binding affinity for the intestinal receptor is lower than that of $1,25(OH)_2D_3$. In vivo in rats the compounds are less active than $1,25(OH)_2D_3$ in inducing hypercalciuria and hypercalcemia.

This renders the compounds of the invention especially suited for both local and systemic treatment and prophylaxis of human and veterinary disorders which are characterized by abnormal cell proliferation and/or cell differentiation, such as certain dermatological disorders including psoriasis and certain cancer forms, e.g. leukemia and myelofibrosis, and diseases characterized by an imbalance in the immune system, e.g autoimmune diseases, or AIDS, and to obtain desired immunosuppression as in transplantation procedures, as well as treatment of acne, diabetes mellitus and hypertension and inflammatory diseases, such as rheumatoid arthritis and asthma. As the compounds of this invention may promote the differentiation of the hair follicle cells, these compounds may be used in the the treatment of alopecia. Preliminary studies indicate that the compounds of the invention may reverse the unattractive concomitants of skin ageing, e.g. on photoaged skin.

The compounds of formula I may conveniently be prepared from the vitamin D-derivative 1 (or its 20R isomer) (Tetrahedron, 43, 4609 (1987)) by the routes outlined in Scheme 2. Oxidation of 1 for example using the van Rheenen procedure (Tetrahedron Lett., 1969, 985) gives the ketone 2, which is reduced to the 20R-alcohol 3. When a suitable chiral reducing agent is used 3 may be prepared with very high stereoselectivity, but 3 is conveniently prepared by $NaBH_4$ reduction of 2 and removing the minor amount of the corresponding 20S-alcohol chromatographically. O-Alkylation of 3 to give III is achieved by treatment under basic conditions with a side chain building block of general formula $Z-R^3$ in which Z is a leaving group such as bromine, iodine, p-toluenesulphonyloxy, methanesulphonyloxy or trifluoromethanesulphonyloxy, and $R^3$ is R (of formula I) or optionally a radical which can be converted to R at any convenient later stage (or over several stages). Thus $R^3$ in compounds III, IV, V and VI does not necessarily have the same meaning along a particular synthetic sequence. The conversion of $R^3$ to R may well involve several steps and possibly involve a temporary protection of the sensitive triene system of the molecule. Apart from any necessary modification within the side chain ($R^3$), the conversion of III to I involves a photoisomerisation step and a desilylation step, analogous to the steps used in the last stages of the synthesis of other vitamin D analogues (see European patent No. 0 227 826).

In general, the side chain fragment $R^3$-Z has the structure

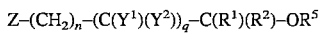

which typically implies that $R^3$ is identical with formula II in which X is a protected OH group ($R^5$ e.g.=tetrahydropyranyl or trialkylsilyl). The leaving group, Z, should be chosen in such a way that it is more reactive than the substituents $Y^1$ and $Y^2$ or corresponding heteroatoms in $R^1$ and $R^2$.

The side chain building blocks are either known compounds (illustrated by (R)- and (S)-4-(1-ethoxyethoxy)-3-fluoro-1-iodo-4-methylpentane described in S. -J. Shiney et al, J. Org. Chem., 53, 1040 (1988) and 4-(1-ethoxyethoxy)-3,3-difluoro-1-iodo-4-methylpentane described in J. J. Partridge et al, U.S. Pat. No. 4,421,690) or may be prepared by the routes outlined in Scheme 1. It is obvious that the syntheses of the particular fragments can be varied greatly, but solely for the purpose of exemplification, the syntheses of the specific compounds shown in Table 1 are described in the Preparations.

The following standard abbreviations are used throughout this disclosure: Me=methyl; Et=ethyl; $Pr^n$=n-propyl; $pr^i$=isopropyl; $Bu^t$=tert-butyl; MOM=methoxymethyl; EE=1-ethoxyethyl; THP=tetrahydro-4H-pyran-2-yl; THF=tetrahydrofuran: Ts=p-toluenesulphonyl; TBA=tetra-(n-butyl)-ammonium; TMS=trimethylsilyl; TBDMS=tert-butyldimethylsilyl; DMF=dimethylformamide.

Scheme 1

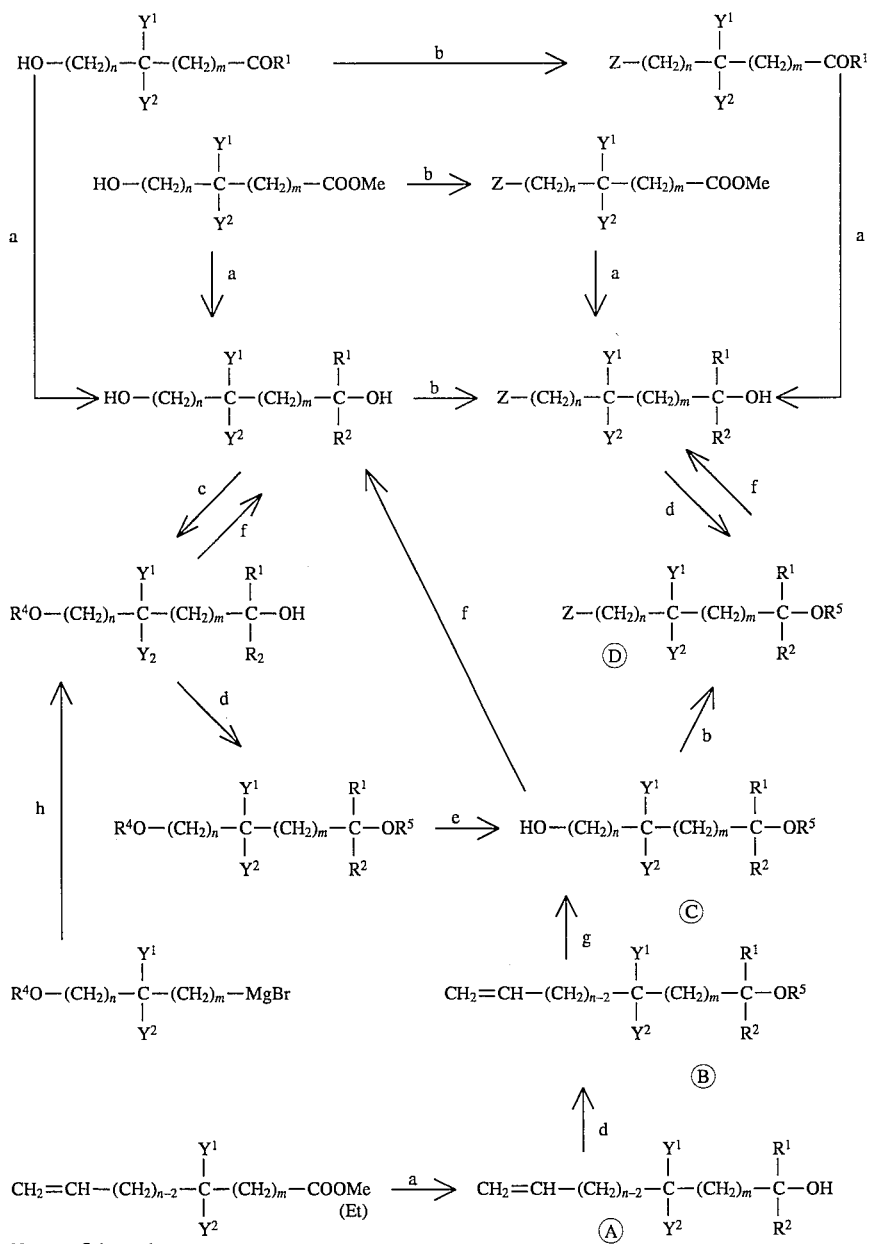

Notes to Scheme 1 a) Reaction with an organometallic reagent (e.g. $R^2MgBr$, $R^2MgI$ or $R^2Li$).
b) Conversion of OH to a leaving group (e.g. by tosylation for Z = OTs or bromination for Z = Br).
c) Selective protection of the primary alcohol group ($R^4$ is typically an acetate or benzoate group).
d) Protection of the hydroxyl group (e.g. tri(loweralkyl)silyl, MOM or THP).
e) Selective deprotection of the primary alcohol group (e.g. $K_2CO_3$ or $LiAlH_4$).
f) Deprotection of the hydroxyl group (e.g. $TBA^+F^-$ or HF).
g) Hydroboration-oxidation (borane complex + alkaline peroxide).
h) Grignard reaction with a ketone of formula $R^1-CO-R^2$.

Scheme 2

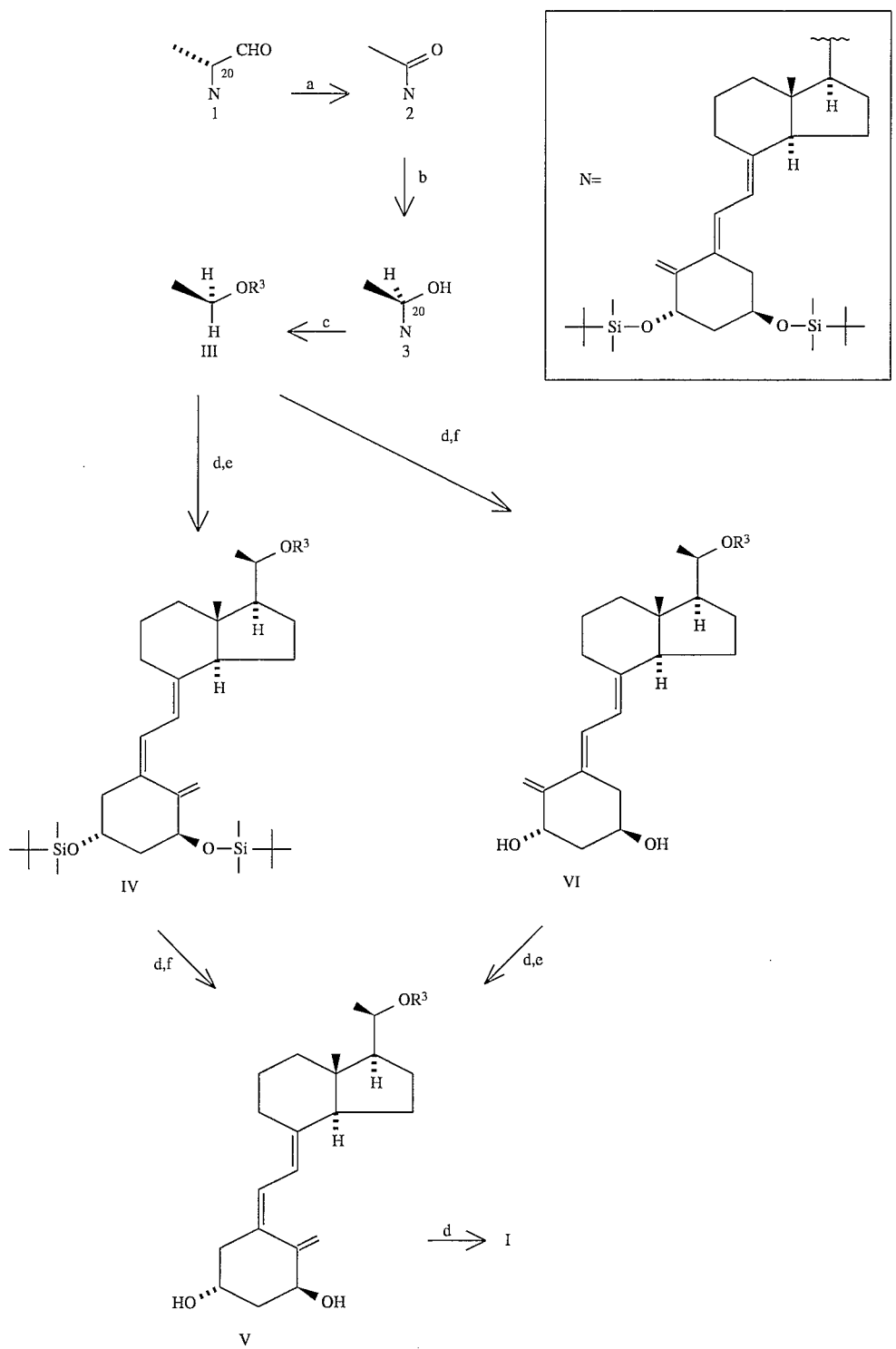

Notes to Scheme 2 a) Oxidation e.g. with $O_2$ with $Cu(AcO)_2$, 2,2'-bipyridyl and 1,4-diazabicyclo[2,2,2]octane as catalyst.
b) Reduction (e.g. with $NaBH_4$).
c) Alkylation with the side chain fragment $R^3$—Z in the presence of base (e.g. KOH, KOBu$^t$ or KH, with or without catalyst (e.g. 18-Crown-6) in solvent, e.g. THF.
d) Optional functional group modification in the side chain.
e) Isomerisation with hv-triplet sensitizer, e.g. anthracene.
f) Deprotection with TBA$^+$F$^-$ or HF.

It should be noted that although the shown intermediates may have hydroxyl groups protected as tert-butyldimethylsilyl ethers, the scope of the invention does not exclude the use of alternative hydroxyl protecting groups well known in the art (such as those described in T. W. Greene, "Protective groups in organic synthesis", Wiley, New York, 1981), together with alternative reactions for deprotection.

The present compounds are intended for use in pharmaceutical compositions which are useful in the treatment of human and veterinary disorders as described above.

The amount required of a compound of formula I (hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders. In the treatment of dermatological disorders like psoriasis, topical or enteral forms are preferred.

In the treatment of respiratory diseases like asthma an aerosol is preferred.

While it is possible for an active ingredient to be administered alone as the raw chemical, it is preferable to present it as a pharmaceutical formulation. Conveniently, the active ingredient comprises from 1 ppm to 0.1% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include e.g. those in a form suitable for oral, rectal, parenteral (including subcutaneous, intramuscular and intravenous), intra-articular, topical, and intraocular administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredients. Compressed tablets may be prepared by compressing, in a suitable machine, the active ingredient in a free-flowing form such as a powder or granules, optionally mixed by a binder, lubricant, inert diluent, surface active or dispersing agent. Moulded tablets may be made by moulding, in a suitable machine, a mixture of the powdered active ingredient and suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration, including eye formulations, include liquid or semi-liquid preparations such as liniments, lotions, applicants, oil-in-water or water-in-oil emulsions such as creams, ointments, including eye ointments, pastes; or solutions or suspensions such as drops, including eye-drops.

For asthma treatment inhalation of powder, self-propelling or spray formulations, dispensed with a spray can, a nebulizer or an atomizer can be used. The formulations, when dispensed, preferably have a particle size in the range of 10 to 100 μ.

Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$-$C_6$ hydrocarbons or halogenated $C_1$-$C_6$ hydrocarbons or mixtures thereof; chlorinated and flourinated $C_1$-$C_6$ hydrocarbons are especially preferred. Generally, the propellant constitutes 45 to 99.9% w/w of the formulation whilst the active ingredient constitutes 1 ppm to 0.1% w/w, of the formulation.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including antioxidants), emulsifying agents and the like.

The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders daily doses of from 0.1–100 µg, preferably from 0.2–25 µg, of a compound of formula I are administered. In the topical treatment of dermatological disorders, ointments, creams or lotions containing from 0.1–500 µg/g, and preferably from 1–100 µg/g, of a compound of formula I are administered. The oral compositions are formulated, preferably as tablets, capsules, or drops, containing from 0.05–50 µg, preferably from 0.1–25 µg, of a compound of formula I, per dosage unit.

The invention will now be further described in the following non-limiting Preparations and Examples:

PREPARATIONS AND EXAMPLES

General

The exemplified Compounds I are listed in Table 1. The side chain fragments of Scheme 1 and the intermediates of Scheme 2 referred to in the Preparations are to be identified by numbers with the corresponding formulae in Table 2 and 3, respectively. These are used to illustrate typical syntheses of the exemplified Compounds I.

For nuclear magnetic resonance spectra (300 MHz) chemical shift values ($\delta$) are quoted for deuteriochloroform solutions relative to internal tetramethylsilane ($\delta$=0) or chloroform ($\delta$=7.25). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit.

Ether is diethyl ether, and was dried over sodium. THF was dried over sodium-benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue.

TABLE 1

Examples of Compounds of Formula I (Details are Provided for Compounds where an Example Number is given; the other Compounds may be prepared using analogous Reaction Sequences)

| Comp. No. | Example No. | n | q | m | $Y^1$ | $Y^2$ | $R^1$ | $R^2$ | X |
|---|---|---|---|---|---|---|---|---|---|
| 101 | | 1 | 1 | 0 | F | F | Et | Et | OH |
| 102 | | 2 | 1 | 0 | F | F | Me | Me | OH |
| 103 | | 2 | 1 | 0 | F | F | Et | Et | OH |
| 104* | | 2 | 1 | 0 | F | H | Me | Me | OH |
| 105+ | | 2 | 1 | 0 | H | F | Me | Me | OH |
| 106* | | 2 | 1 | 0 | F | H | Et | Et | OH |
| 107+ | | 2 | 1 | 0 | H | F | Et | Et | OH |
| 108 | 1 | 3 | 1 | 0 | F | F | Me | Me | OH |
| 109 | 2 | 3 | 1 | 0 | F | F | Et | Et | OH |
| 110 | | 4 | 1 | 0 | F | F | Et | Et | OH |
| 111 | | 1 | 1 | 1 | F | F | Et | Et | OH |
| 112 | | 2 | 1 | 1 | F | F | Me | Me | OH |
| 113 | | 2 | 1 | 1 | F | F | Et | Et | OH |
| 114 | | 2 | 1 | 0 | F | F | Et | Et | H |
| 115 | | 3 | 1 | 0 | F | F | Et | Et | H |
| 116 | 4 | 2 | 0 | 0 | — | — | 2-fluoropropyl-2 | H | H |
| 117 | 5 | 2 | 0 | 0 | — | — | 3-fluoropentyl-3 | H | H |
| 118 | 6 | 3 | 0 | 0 | — | — | 2-fluoropropyl-2 | H | H |
| 119 | 7 | 3 | 0 | 0 | — | — | 3-fluoropentyl-3 | H | H |
| 120 | | 2 | 1 | 0 | F | F | $CF_3$ | $CF_3$ | OH |
| 121 | | 2 | 1 | 0 | F | F | $CF_2CF_3$ | $CF_2CF_3$ | OH |
| 122 | | 3 | 0 | 0 | — | — | $CF_3$ | $CF_3$ | OH |
| 123 | | 3 | 0 | 0 | — | — | $CF_2CF_3$ | $CF_2CF_3$ | OH |
| 124 | | 3 | 0 | 0 | — | — | $CH_2CF_3$ | $CH_2CF_3$ | OH |
| 125 | | 3 | 1 | 0 | F | F | Me | Me | OH |
| 126 | | 4 | 0 | 0 | — | — | Me | Me | OH |
| 127 | | 2 | 1 | 0 | Cl | Cl | Me | Me | OH |
| 128 | | 2 | 1 | 0 | Cl | Cl | Et | Et | OH |
| 129 | 3 | 3 | 1 | 0 | Cl | Cl | Me | Me | OH |
| 130 | | 3 | 1 | 0 | Cl | Cl | Et | Et | OH |
| 131 | | 2 | 1 | 1 | Cl | Cl | Et | Et | OH |
| 132 | | 2 | 1 | 0 | Cl | Cl | Et | Et | OH |
| 133 | | 2 | 1 | 0 | Br | Br | Et | Et | OH |
| 134 | 8 | 3 | 0 | 0 | — | — | $CH_2N_3$ | H | H |
| 135 | 9 | 4 | 0 | 0 | — | — | $CH_2N_3$ | H | H |

*R-configuration
+S-configuration

TABLE 2

Some Specific Side Chain Fragments

| Comp. No. | Prep. No. | Type* | n | m | Y¹ | Y² | R¹ | R² | R⁵ | Z |
|---|---|---|---|---|---|---|---|---|---|---|
| 4 | 3 | A | 3 | 0 | F | F | Me | Me | H | — |
| 5 | 4 | B | 3 | 0 | F | F | Me | Me | THP | — |
| 6 | 5 | C | 3 | 0 | F | F | Me | Me | THP | — |
| 7 | 6 | D | 3 | 0 | F | F | Me | Me | THP | TsO |
| 8 | 7 | A | 3 | 0 | F | F | Et | Et | H | — |
| 9 | 8 | B | 3 | 0 | F | F | Et | Et | MOM | — |
| 10 | 9 | C | 3 | 0 | F | F | Et | Et | MOM | — |
| 11 | 10 | D | 3 | 0 | F | F | Et | Et | MOM | TsO |
| 12 | 11 | A | 3 | 0 | Cl | Cl | Me | Me | H | — |
| 13 | 12 | B | 3 | 0 | Cl | Cl | Me | Me | THP | — |
| 14 | 13 | C | 3 | 0 | Cl | Cl | Me | Me | THP | — |
| 15 | 14 | D | 3 | 0 | Cl | Cl | Me | Me | THP | TsO |
| 16 | 15 | B | 3 | 0 | F | F | Et | Et | SiEt₃ | — |
| 17 | 16 | C | 2 | 0 | F | F | Et | Et | SiEt₃ | — |
| 18 | 17 | C | 2 | 0 | Cl | Cl | Me | Me | THP | — |

*See Scheme 1

TABLE 3

Some specific Examples of Intermediates of Formula III and IV (Scheme 2) which are referred to by Numbers in the Preparations

| Comp. No. | Prep. No. | Type | n | q | m | Y¹ | Y² | R¹ | R² | X¹ |
|---|---|---|---|---|---|---|---|---|---|---|
| 23 | 22 | III | 3 | 1 | 0 | F | F | Me | Me | OTHP |
| 24 | 23 | III | 3 | 1 | 0 | F | F | Et | Et | OMOM |
| 25 | 24 | III | 3 | 1 | 0 | Cl | Cl | Me | Me | OTHP |
| 26 | 25 | III | 2 | 0 | 0 | — | — | 2-fluoropropyl-2 | H | H |
| 27 | 26 | III | 2 | 0 | 0 | — | — | 3-fluoropentyl-3 | H | H |
| 28 | 27 | III | 3 | 0 | 0 | — | — | 2-fluoropropyl-2 | H | H |
| 29 | 28 | III | 3 | 0 | 0 | — | — | 3-fluoropentyl-3 | H | H |
| 30 | 29 | III | 3 | 0 | 0 | — | — | CH₂Cl | H | H |
| 31 | 30 | III | 4 | 0 | 0 | — | — | CH₂Cl | H | H |
| 32 | 31 | III | 2 | 1 | 0 | F | F | Me | Me | OEE |
| 33* | 32 | III | 2 | 1 | 0 | F | H | Me | Me | OEE |
| 34⁺ | 33 | III | 2 | 1 | 0 | H | F | Me | Me | OEE |
| 35 | 34 | III | 2 | 1 | 0 | F | F | Et | Et | OSiEt₃ |
| 36 | 35 | III | 2 | 1 | 0 | Cl | Cl | Me | Me | OTHP |
| 37 | 36 | IV | 3 | 1 | 0 | F | F | Me | Me | OTHP |
| 38 | 37 | IV | 3 | 1 | 0 | F | F | Et | Et | OMOM |
| 39 | 38 | IV | 3 | 1 | 0 | Cl | Cl | Me | Me | OTHP |
| 40 | 39 | IV | 2 | 0 | 0 | — | — | 2-fluoropropyl-2 | H | H |
| 41 | 40 | IV | 2 | 0 | 0 | — | — | 3-fluoropentyl-3 | H | H |
| 42 | 41 | IV | 3 | 0 | 0 | — | — | 2-fluoropropyl-2 | H | H |
| 43 | 42 | IV | 3 | 0 | 0 | — | — | 3-fluoropentyl-3 | H | H |
| 44 | 43 | IV | 3 | 0 | 0 | — | — | CH₂Cl | H | H |
| 45 | 44 | IV | 4 | 0 | 0 | — | — | CH₂Cl | H | H |
| 46 | 45 | IV | 2 | 1 | 0 | F | F | Me | Me | OEE |
| 47* | 46 | IV | 2 | 1 | 0 | F | H | Me | Me | OEE |
| 48⁺ | 47 | IV | 2 | 1 | 0 | H | F | Me | Me | OEE |
| 49 | 48 | IV | 2 | 1 | 0 | F | F | Et | Et | OSiEt₃ |
| 50 | 49 | IV | 2 | 1 | 0 | Cl | Cl | Me | Me | OTHP |
| 51 | 50 | IV | 3 | 0 | 0 | — | — | CH₂N₃ | H | H |
| 52 | 51 | IV | 4 | 0 | 0 | — | — | CH₂N₃ | H | H |

*R-configuration
⁺S-configuration

PREPARATION 1

Compound 2

To a solution of 1(S), 3(R)-bis-(tert-butyldimethylsilyloxy)-20(S)-formyl-9,10-secopregna-5(E), (7E), 10(19)-triene (3.44 g, 6 mmol) (1) in N,N-dimethylformamide (150 ml), 1,4-diazabicyclo[2.2.2]octane (600 mg, 5.3 mmol), cupric acetate, monohydrate (90 mg, 0.45 mmol) and 2,2'-bipyridyl (72 mg, 0.45 mmol) were added. Air was bubbled through the well stirred solution for 6 days at 40° C.

The reaction mixture was diluted with ethyl acetate (500 ml), extracted with water (2×100 ml) and saturated aqueous sodium chloride (3×50 ml) and dried over MgSO₄. Ethyl acetate was evaporated off, and the solid residue was purified by chromatography (silica gel, 10% ether in petroleum ether as eluant) to give the title compound.

NMR: δ=0.037 (s, 3H), 0.043 (s, 3H), 0.056 (s, 6H), 0.49 (s, 3H), 0.84 (s, 9H), 0.89 (s, 9H), 1.5–2.30 (m, 13H), 2.13 (s, 3H), 2.55 (dd, 1H), 2.70 (t, 1H), 2.89 (bd, 1H), 4.21 (m, 1H), 4.52 (m, 1H), 4.94 (m, 1H), 4.98 (m, 1H), 5.83 (d, 1H), 6.43 (d, 1H) ppm.

PREPARATION 2

Compound 3 and its 20S-isomer

Compound 2 (Prep. 1) (3.10 g, 5.5 mmol) was dissolved in tetrahydrofuran ( 140 ml ) and sodium borohydride ( 0.35 g, 3.3 mmol) was added. Methanol was then added dropwise over 15 minutes. The reaction blend was stirred for 20 minutes, then diluted with ethyl acetate (560 ml). The solution was extracted with water (5×150 ml) and saturated aqueous sodium chloride (150 ml), dried over $MgSO_4$ and evaporated to give a colourless oil. The oily residue was purified by chromatography (silica gel, 15% ethyl acetate in petroleum ether as eluant) and crystallization from methanol to give 3.

NMR: δ=0.05 (m, 12H), 0.62 (s, 3H), 0.86 (s, 9H), 0.89 (s, 9H), 1.10–2.10 (m, 14H), 1.15 (d, 3H), 2.30 (bd, 1H), 2.53 (dd, 1H), 2.89 (m, 1H), 2.89 (m, 1H), 3.71 (m, 1H), 4.21 (m, 1H), 4.52 (m, 1H), 4.93 (m, 1H), 4.98 (m, 1H), 5.81 (d, 1H), 6.45 (d, 1H) ppm.

The fractions containing the more polar 20S-isomer were evaporated to give a colourless residue which was crystallized from methanol:

NMR, δ=0.052 (bd, 12H), 0.54 (s, 3H), 0.85 (s, 9H), 0.89 (s, 9H), 1.22 (d, 3H), 1.20–2.10 (m, 14H), 2.30 (bd, 1H), 2.55 (dd, 1H), 2.87 (m, 1H), 3.72 (m, 1H), 4.21 (m, 1H), 4.52 (m, 1H), 4.94 (bs, 1H), 4.98 (m, 1H), 5.82 (d, 1H), 6.44 (d, 1H) ppm.

PREPARATION 3

3,3-Difluoro-2-methyl-5-hexen-2-ol (Compound 4)

To a solution of ethyl 2,2-difluoro-4-pentenoate (5.0 g, 30.5 mmol) in dry ether (50 ml) at –25° was added dropwise a solution of methyl magnesium bromide (3.0M; 30.5 ml). The mixture was stirred at -25° C. for half an hour and at 0° C. for 1 hour. The reaction mixture is poured into a saturated aqueous $NH_4Cl$ solution (25 ml). The phases were separated and the aqueous phase was extracted with more ether (2×25 ml). The combined organic phases were dried with $MgSO_4$ and concentrated. Flash chromatography (50 g silica gel, 5% ether in petroleum ether as eluant) to give the title compound as a colourless oil.

NMR: δ=1.32 (t, 6H), 1.97 (bs, 1H), 2.74 (m, 2H), 5.20 (m, 2H), 5.92 (m, 1H) ppm.

PREPARATION 4

3,3-Difluoro-2-methyl-2-[(tetrahydro-2H-pyran-2-yl)oxy]-5-hexene (Compound 5)

A solution of Compound 4 (3.8 g, 25.3 mmol) and freshly distilled 3,4-dihydro-2H-pyran (4.59 ml, 50.6 mmol) in dichloromethane (50 ml) are stirred at room temperature in the presence of acidic silica gel (150 mg). After stirring for 1 hour the catalyst is removed by filtration and 1–2 drops of triethylamine are added. The solvent is removed under reduced pressure, and the residue is purified by column chromatography (50 g silica gel, 5% ether in petroleum ether as eluant) to give the compound as a colourless oil.

NMR: δ=1.35 (t, 6H), 1.53 (m, 4H), 1.69 (m, 1H), 1.84 (m, 1H), 2.74 (m, 2H), 3.48 (m, 1H), 3.94 (m, 1H), 4.90 (m, 1H), 5.19 (m, 2H), 5.91 (m, 1H) ppm.

PREPARATION 5

4,4-Difluoro-5-methyl-5-[(tetrahydro-2H-pyran-2-Yl)oxy]-1-hexanol (Compound 6)

Borane-methyl sulfide complex (21.3 ml, 0.213 mol) was added to a stirred solution of Compound 5 (5.0 g, 21.3 mmol) in dry THF (100 ml), at 0° C. under argon. The reaction was stirred 2 hours at 0° C., and treated sequentially with water (20 ml), NaOH (3M; 55 ml), and $H_2O_2$ (30% aqueous solution; 30 ml). This mixture was stirred for 1 hour at 25° C., diluted with water (150 ml), extracted with ether, and washed with saturated $NaHCO_3$ and brine. The organic layer was dried over $MgSO_4$, the solvent was removed vacuo, and the crude product was examined by $^1H$ NMR spectroscopy which showed the ratio between the desired compound and the corresponding Markovnikov product to be 71:29. The mixture was purified by flash chromatography (50 g silica gel, 10% to 20% ethyl acetate in petroleum ether as eluant) to give the pure primary alcohol as a colourless oil.

NMR: δ=1.34 (bs, 6H), 1.53 (m, 4H), 1.68 (m, 1H), 1.82 (m, 4H), 1.92–2.17 (m, 2H), 3.48 (m, 1H), 3.70 (bt, 2H), 3.93 (m, 1H), 4.89 (m, 1H) ppm.

PREPARATION 6

4,4-Difluoro-5-methyl-5-[(tenrahydro-2H-pyran-2-yl)oxy]-1-(4-toluenesulphonyloxy)-hexane (Compound 7)

Compound 6 (2.85 g, 11.3 mmol) was dissolved in dichloromethane (75 ml) and pyridine (10 ml), and the solution was stirred and ice-cooled during the addition of p-toluenesulfonyl chloride (7.11 g, 37.3 mmol). The reaction mixture was allowed to stand at room temperature overnight before being partitioned between ethyl acetate and water. The organic layer was washed consecutively with saturated hydrogen carbonate solution, water, and brine, and then dried and concentrated in vacuo. Flash chromatography (50 g silica gel, 5% ethyl acetate in petroleum ether as eluant) to give the desired tosylate as an oil.

NMR: δ=1.30 (bs, 6H), 1.40–2.12 (m, 10H), 2.45 (s, 3H), 3.47 (m, 1H), 3.90 (m, 1H), 4.10 (t, 2H), 4.85 (m, 1H), 7.35 (d, 2H), 7.79 (d, 2H) ppm.

PREPARATION 7

3-Ethyl-4,4-difluoro-6-hepten-3-ol (Compound 8)

To a solution of ethyl 2,2-difluoro-4-pentenoate (5.0 g, 30.5 mmol) in dry ether (50 ml) at −78° C. was added dropwise a solution of ethyl lithium (1.7M; 35.9 ml). After stirring for 30 minutes at −78° C. saturated aqueous NH₄Cl solution (25 ml) was added. The phases were separated and the aqueous phase was extracted twice with ether (25 ml). The combined ether layers are washed consecutively with water (2×50 ml) and saturated aqueous sodium chloride (50 ml), dried and concentrated in vacuo. Flash chromatography (75 g silica gel, 5% to 10% ethyl acetate in petroleum ether as eluant) gave the title compound as a colourless oil.

NMR: δ=0.94 (m, 6H), 1.68 (m, 4H), 1.76 (s, 1H), 2.73 (m, 2H), 5.20 (m, 2H), 5.93 (m, 1H) ppm.

PREPARATION 8

3-Ethyl-4,4-difluoro-3-O-methoxymethyl-6-hepten (Compound 9)

To a stirred solution of Compound 8 (2.83 g, 15.9 mmol) in dry chloroform (100 ml) were added methylal (75 ml) and phosphorus pentoxide (25 g). After stirring for 2 hours the mixture was poured into an ice-cooled sodium carbonate solution. The organic phase is isolated and washed with brine, dried over calcium chloride, and evaporated in vacuo. The residue is purified by chromatography (75 g silica gel, 5% to 10% ethyl acetate in petroleum ether as eluant) to give the desired compound as an oil.

NMR: δ=0.95 (m, 6H), 1.79 (m, 4H), 2.71 (m, 2H), 3.40 (s, 3H), 4.76 (s, 2H), 5.20 (m, 2H), 5.90 (m, 1H) ppm.

PREPARATION 9

5-Ethyl-4,4-difluoro-5-O-methoxymethyl-1-heptanol (Compound 10)

The compound was prepared using the method of Preparation 5, except using Compound 9 as starting material instead of Compound 5.

NMR: δ=0.94 (bt, 6H), 1.60–2.13 (m, 8H), 2.56 (bs, 1H), 3.40 (s, 3H), 3.67 (t, 2H), 4.75 (s, 2H) ppm.

PREPARATION 10

5-Ethyl-4,4-difluoro-5-O-methoxymethyl-1-(4-toluenesulphonyloxy)-heptane (Compound 11)

The compound was prepared using the method of Preparation 6, except using Compound 10 as starting material instead of Compound 6.

NMR: δ=0.92 (bt, 6H), 1.60–2.10 (m, 8H), 2.45 (bs, 3H), 3.38 (s, 3H), 4.09 (t, 2H), 4.70 (s, 2H), 7.35 (d, 2H), 7.79 (d, 2H) ppm.

PREPARATION 11

3,3-Dichloro-2-methyl-5-hexen-2-ol (Compound 12)

The compound was prepared using the method of Preparation 3, except using methyl 2,2-dichloro-4-pentenoate as starting material instead of ethyl 2,2-difluoro-4-pentenoate.

NMR: δ=1.54 (s, 6H), 2.27 (bs, 1H), 3.02 (m, 2H), 5.27 (m, 2H), 6.11 (m, 1H) ppm.

PREPARATION 12

3,3-Dichloro-2-methyl-2, [(tetrahydro-2H-pyran-2-yl)oxy]-5-hexene (Compound 13)

The compound was prepared using the method of Preparation 4, except using Compound 12 as starting material instead of Compound 4.

NMR: δ=1.57 (s, 3H), 1.60 (s, 3H), 1.50–1.90 (m, 6H), 2.92–3.15 (m, 2H), 3.51 (m, 1H), 3.97 (m, 1H), 5.00 (m, 1H), 5.17–5.32 (m, 2H), 6.13 (m, 1H) ppm.

PREPARATION 13

4,4-Dichloro-5-methyl-5-[(tetrahydro-2H-pyran-2-yl)oxy]-1-hexanol (Compound 14)

The compound was prepared using the method of Preparation 5, except using Compound 13 as starting material instead of Compound 5.

NMR: δ=1.56 (s, 3H), 1.60 (s, 3H), 1.50–2.15 (m, 9H), 2.35 (m, 2H), 3.50 (m, 1H), 3.75 (m, 2H), 3.97 (m, 1H), 4.99 (m, 1H) ppm.

PREPARATION 14

4,4-Dichloro-5-methyl-5-[(tetrahydro-2H-pyran-2-yl)oxy]-1-(4-toluenesulphonyloxy)-hexane (Compound 15)

The compound was prepared using the method of Preparation 6, except using Compound 14 as starting material instead of Compound 6.

NMR: δ=1.51 (s, 3H), 1.56 (s, 3H), 1.50–2.42 (m, 10H), 2.45 (s, 3H), 3.50 (m, 1H), 3.94 (m, 1H), 4.15 (t, 2H), 4.95 (m, 1H), 7.36 (d, 2H), 7.80 (m, 2H) ppm.

PREPARATION 15

3-Ethyl-4,4-difluoro-3-triethylsilyloxy-6-hepten (Compound 16)

To a stirred solution of Compound 8 (1.7 g, 9.54 mmol) in dichloromethane (10 ml) at 0° C. were added 2,6-lutidine (2.26 ml, 19.1 mmol) and triethylsilyl trifluoromethanesulfonate (2.37 ml, 10.5 mmol), and the mixture is stirred for 1 hour at room temperature. Ether (50 ml) and water (75 ml) are added. The organic phase is isolated, washed with water (2×50 ml) and saturated aqueous sodium chloride (50 ml), dried, and evaporated in vacuo. The crude product is purified by chromatography (50 g silica gel; 1% ethyl acetate in petroleum ether as eluant) to yield the desired compound as an oil.

NMR: δ=0.62 (q, 6H), 0.95 (t, 9H), 0.85–1.00 (m, 6H), 1.50–1.85 (m, 4H), 2.68 (m, 2H), 5.10–5.25 (m, 2H), 5.91 (m, 1H) ppm.

PREPARATION 16

4-Ethyl-3,3-difluoro-4-triethylsilyloxy-1-hexanol (Compound 17)

Compound 16 (1.41 g, 4.82 mmol) was dissolved in dichloromethane (100 ml), and the solution was cooled to −78° C. A gaseous mixture of $O_3$ in $O_2$ was passed into the solution until it became light blue in colour. Nitrogen was bubbled through the solution to remove excess ozone, dimethyl sulfide (2 ml) was added, and the solution was brought slowly to room temperature. The organic layer was washed with water (twice), dried over $CaCl_2$ and concentrated under reduced pressure.

To a stirred, ice-cooled solution of the crude aldehyde in THF (3 ml) and ethanol (10 ml) was added sodium borohydride (219 mg, 5.78 mmol). After half an hour the reaction mixture was partitioned between ethyl acetate and water, and the organic layer was washed with brine, dried over $MgSO_4$ and concentrated. Flash chromatography (50 g silica gel; 10% ethyl acetate in petroleum ether as eluant) afforded the desired compound as a colourless oil.

NMR: δ=0.61 (q, 6H), 0.93 (t, 9H), 0.85–1.00 (m, 6H), 1.50–1.82 (m, 4H), 1.91 (bt, 1H), 2.19 (m, 2H), 3.87 (q, 2H) ppm.

PREPARATION 17

3,3-Dichloro-4-methyl-4-[(tetrahydro-2H-pyran-2-yl)oxy]-1-pentanol (Compound 18)

The compound was prepared using the method of Preparation 16, except using Compound 13 as starting material instead of Compound 16.

NMR: δ=1.57 (s, 3H), 1.61 (s, 3H), 1.50–1.95 (m, 6H), 2.52–2.77 (m, 3H), 3.52 (m, 1H), 3.90–4.15 (m, 3H), 4.97 (m, 1H) ppm.

PREPARATION 18

1-Bromo-4-fluoro-4-methyl-pentane (Compound 19)

To a solution of diethylaminosulfur trifluoride (DAST) (7.78 ml, 59.3 mmol) in dry dichloromethane (25 ml) at −70° C. was added dropwise 5-bromo-2-methyl-2-pentanol (7.15 g, 39.5 mmol) in dry dichloromethane (25 ml). The mixture was stirred at −70° C. for 1 hour, at 0° C. for 0.5 hour, and at room temperature for 1 hour. The mixture was slowly poured into a saturated aqueous sodium bicarbonate solution at 0° C., and the product was extracted with dichloromethane. The organic phase was dried ($MgSO_4$), filtered, and evaporated to dryness. The residue was purified by column chromatography (30 g silica gel, 5% ethyl acetate in petroleum ether as eluant) to give 5.94 g (82%) of the desired compound as a colourless oil.

NMR: δ=1.33 (s, 3H), 1.40 (s, 3H), 1.75 (m, 2H), 1.98 (m, 2H), 3.43 (t, 2H) ppm.

PREPARATION 19

1-Chloro-4-ethyl-4-fluoro-hexane (Compound 20)

The compound was prepared using the method of Preparation 18, except using 6-chloro-3-ethyl-3-hexanol as starting material instead of 5-bromo-2-methyl-2-pentanol.

NMR: δ=0.90 (t, 6H), 1.55–1.92 (m, 8H), 3.56 (t, 2H) ppm.

PREPARATION 20

1-Bromo-5-fluoro-5-methyl-hexane (Compound 21)

The compound was prepared using the method of Preparation 18, except using 6-bromo-2-methyl-2-hexanol as starting material instead of 5-bromo-2-methyl-2-pentanol.

NMR: δ=1.35 (d, J=21.4 Hz, 6H), 1.50–1.70 (m, 4H), 1.88 (m, 2H), 3.43 (t, 2H) ppm.

PREPARATION 21

1-Bromo-5-methyl-5-fluoro-heptane (Compound 22)

The compound was prepared using the method of Preparation 18, except using 7-bromo-3-ethyl-3-heptanol as starting material instead of 5-bromo-2-methyl-2-pentanol.

NMR: δ=0.89 (t, 6H), 1.45–1.72 (m, 8H), 1.88 (m, 2H), 3.43 (t, 2H) ppm.

GENERAL PROCEDURE 1

O-Alkylation of Compound 3 to give Compound III

To a solution stirred under argon of Compound 3 (1.0 mmol) in dry THF (10 ml) were added sequentially potassium hydride (0.4 ml, 20% suspension in oil), 18-Crown-6 (264 mg) and the requisite alkylating agent $R^3$-Z. The mixture is stirred at room temperature for 2 hours, diluted with ether (100 ml) and extracted with water (3×50 ml) and saturated aqueous sodium chloride (50 ml). After drying and the removal of the solvent in vacuo, the product is purified by chromatography (silica gel; 10% ether in petroleum ether as eluant) to give the Compound III.

PREPARATION 22

Compound 23

Method: General Procedure 1

Alkylating agent: Compound 7

NMR: δ=0.06 (m, 12H), 0.55 (s, 3H), 0.86 (s, 9H), 0.89 (s, 9H), 1.08 (d, 3H), 1.32 (bs, 6H), 1.05–2.20 (m, 23H), 2.30 (bd, 1H), 2.55 (dd, 1H), 2.86 (bd, 1H), 3.25 (m, 2H), 3.46 (m, 1H), 3.62 (m, 1H), 3.91 (m, 1H), 4.21 (m, 1H), 4.53 (m, 1H), 4.88 (m, 1H), 4.94 (m, 1H), 4.98 (m, 1H), 5.80 (d, 1H), 6.46 (d, 1H) ppm.

PREPARATION 23

Compound 24

Method: General Procedure 1

Alkylating agent: Compound 11

NMR: δ=0.06 (m, 12H), 0.55 (s, 3H), 0.86 (s, 9H), 0.89 (s, 9H), 0.93 (m, 6H), 1.08 (d, 3H), 1.03–2.35 (m, 22H), 2.54 (dd, 1H), 2.86 (bd, 1H), 3.25 (m, 2H), 3.39 (s, 3H), 3.63 (m, 1H), 4.22 (m, 1H), 4.53 (m, 1H), 4.72 (s, 2H), 4.94 (m, 1H), 4.98 (m, 1H), 5.80 (d, 1H), 6.46 (d, 1H) ppm.

PREPARATION 24

Compound 25

Method: General Procedure 1

Alkylating agent: Compound 15

NMR: δ=0.05 (m, 12H), 0.55 (s, 3H), 0.85 (s, 9H), 0.89 (s, 9H), 1.09 (d, 3H), 1.00–2.50 (m, 30H), 2.55 (dd, 1H), 2.86 (bd, 1H), 3.25 (m, 2H), 3.48 (m, 1H), 3.69 (m, 1H), 3.95 (m, 1H), 4.21 (m, 1H), 4.52 (m, 1H), 4.94 (m, 1H), 4.98 (m, 2H), 5.80 (d, 1H), 6.45 (d, 1H) ppm.

PREPARATION 25

Compound 26

Method: General Procedure 1

Alkylating agent: Compound 19

NMR: δ=0.06 (m, 12H), 0.55 (s, 3H), 0.86 (s, 9H), 0.89 (s, 9H), 1.07 (d, 3H), 1.30 (s, 3H), 1.37 (s, 3H), 1.00–1.85 (m, 14H), 1.92 (m, 1H), 2.03 (bt, 1H), 2.14 (bd, 1H), 2.30 (bd, 1H), 2.55 (dd, 1H), 2.87 (bd, 1H), 3.23 (m, 2H), 3.55 (m, 1H), 4.21 (m, 1H), 4.53 (m, 1H), 4.93 (m, 1H), 4.98 (m, 1H), 5.80 (d, 1H), 6.46 (d, 1H) ppm.

PREPARATION 26

Compound 27

Method: General Procedure 1

Alkylating agent: Compound 20

NMR: δ=0.06 (m, 12H), 0.55 (s, 3H), 0.86 (s, 9H), 0.90 (s, 9H), 0.80–0.95 (m, 6H), 1.08 (d, 3H), 1.05–1.98 (m, 19H), 2.03 (bt, 1H), 2.16 (bd, 1H), 2.31 (bd, 1H), 2.55 (dd, 1H), 2.87 (m, 1H), 3.18 (m, 1H), 3.26 (m, 1H), 3.57 (m, 1H), 4.21 (m, 1H), 4.53 (m, 1H), 4.93 (m, 1H), 4.98 (m, 1H), 5.80 (d, 1H), 6.46 (d, 1H) ppm.

PREPARATION 27

Compound 28

Method: General Procedure 1

Alkylating agent: Compound 21

NMR: δ=0.06 (m, 12H), 0.55 (s, 3H), 0.86 (s, 9H), 0.89 (s, 9H), 1.08 (d, 3H), 1.32 (d, J=21.5 Hz, 6H), 1.10–1.85 (m, 16H), 1.92 (m, 1H), 2.03 (bt, 1H), 2.15 (bd, 1H), 2.30 (bd, 1H), 2.55 (dd, 1H), 2.87 (bd, 1H), 3.18 (m, 1H), 3.25 (m, 1H), 3.58 (m, 1H), 4.21 (m, 1H), 4.53 (m, 1H), 4.94 (m, 1H), 4.98 (m, 1H), 5.80 (d, 1H), 6.46 (d, 1H) ppm.

PREPARATION 28

Compound 29

Method: General Procedure 1

Alkylating agent: Compound 22

NMR: δ=0.06 (m, 12H), 0.55 (s, 3H), 0.86 (s, 9H), 0.89 (s, 9H), 0.80–0.92 (m, 6H), 1.07 (d, 3H), 1.10–2.00 (m, 21H), 2.04 (m, 1H), 2.16 (bd, 1H), 2.30 (bd, 1H), 2.55 (dd, 1H), 2.87 (bd, 1H), 3.17 (m, 1H), 3.25 (m, 1H), 3.58 (m, 1H), 4.21 (m, 1H), 4.54 (m, 1H), 4.93 (m, 1H), 4.98 (m, 1H), 5.80 (d, 1H), 6.46 (d, 1H).

PREPARATION 29

Compound 30

Method: General Procedure 1

Alkylating agent: 1-Bromo-5-chloropentane.

M.p.: 74°–75° C.

NMR: δ=0.06 (m, 12H), 0.54 (s, 3H), 0.86 (s, 9H), 0.90 (s, 9H), 1.07 (d, 3H), 1.00–1.86 (m, 16H), 1.92 (m, 1H), 2.04 (t, 1H), 2.13 (bd, 1H), 2.31 (bd, 1H), 2.55 (dd, 1H), 2.87 (bd, 1H), 3.12–3.35 (m, 2H), 3.52 (t, 2H), 3.53 (m, 1H), 4.21 (m, 1H), 4.53 (m, 1H), 4.93 (m, 1H), 4.99 (m, 1H), 5.80 (d, 1H), 6.46 (d, 1H) ppm.

PREPARATION 30

Compound 31

Method: General Procedure 1

Alkylating agent: 6-Chloro-p-methylbenzenesulfonate-1-hexanol.

NMR: δ=0.06 (m, 12H), 0.54 (s, 3H), 0.86 (s, 9H), 0.89 (s, 9H), 1.07 (d, 3H), 1.05–1.85 (m, 18H), 1.91 (m, 1H), 2.03 (bt, 1H), 2.13 (bd, 1H), 2.31 (bd, 1H), 2.55 (dd, 1H), 2.87 (bd, 1H), 3.12–3.32 (m, 2H), 3.53 (t, 2H), 3.54 (m, 1H), 4.21 (m, 1H), 4.53 (m, 1H), 4.94 (m, 1H), 4.98 (m, 1H), 5.80 (d, 1H), 6.46 (d, 1H) ppm.

PREPARATION 31

Compound 32

Method: General Procedure 1

Alkylating agent: 4-(1-ethoxyethoxy)-3,3-difluoro-1-iodo-4-methylpentane.

PREPARATION 32

Compound 33

Method: General Procedure 1

Alkylating agent: (R)-4-(1-ethoxyethoxy)-3-fluoro-1-iodo-4-methylpentane.

PREPARATION 33

Compound 34

Method: General Procedure 1

Alkylating agent: (S)-4-(1-ethoxyethoxy)-3-fluoro-1-iodo-4-methylpentane.

PREPARATION 34

Compound 35

A solution of Compound 17 (889 mg, 3.0 mmol) and pyridine (242 μl, 3.0 mmol) in dichloromethane (20 ml) was slowly added under argon to a solution of trifluoromethanesulfonic anhydride (566 μl, 3.5 mmol) in dichloromethane (20 ml) at 0° C. After stirring for 15 minutes, the solution was quickly washed with water (10 ml). Drying (MgSO$_4$+ NaHCO$_3$) and evaporation of solvent over a few mg of NaHCO$_3$ gave the triflate as a yellowish oil which, due to instability, was immediately used in the following alkylating reaction.

A solution of the above triflate in dry THF (5 ml) was added dropwise Via a syringe to a mixture of Compound 3 (561 mg, 1.0 mmol), potassium hydride (0.4 ml, 20% suspension in oil) and 18-Crown-6 (264 mg, 1.0 mmol) in dry THF (10 ml). The resulting solution was stirred under argon for 1 hour, diluted with ether (100 ml) and extracted with water (2×50 ml) and saturated aqueous sodium chloride (50 ml). After drying and removal of the solvent in vacuo, the product is purified by chromatography (silica gel, 5% ether in petroleum ether as eluant) to give the desired compound as a colourless oil.

PREPARATION 35

Compound 36

The compound was prepared using the method of Preparation 34, except using Compound 18 as starting material instead of Compound 17.

GENERAL PROCEDURE 2

Isomerization of Compound III to the Corresponding Compounds IV

A solution of the Compound III (ca. 0.2 g), anthracene (200 mg) and triethylamine (2 drops) in dichloromethane (15 ml) under nitrogen in a Pyrex flask was irradiated with light from a high pressure ultraviolet lamp, type TQ718Z2 (Hanau) at about 10° C. for 30 minutes. The solution is filtered and concentrated in vacuo, and the residue is purified by chromatography to give the Compound IV.

PREPARATION 36

Compound 37

Method: General Procedure 2

Starting material: Compound 23

Chromatography eluant: 2 to 5% ethyl acetate in petroleum ether.

NMR: δ=0.05 (m, 12H), 0.53 (s, 3H), 0.87 (s, 18H), 1.06 (d, 3H), 1.31 (bs, 6H), 1.02–2.25 (m, 24H), 2.44 (dd, 1H), 2.81 (bd, 1H). 3.23 (m, 2H), 3.46 (m, 1H), 3.61 (m, 1H), 3.91 (m, 1H), 4.18 (m, 1H), 4.36 (m, 1H), 4.85 (m, 1H), 4.88 (m, 1H), 5.16 (m, 1H), 5.99 (d, 1H), 6.23 (d, 1H) ppm.

PREPARATION 37

Compound 38

Method: General Procedure 2

Starting material: Compound 24

Chromatography eluant: 2 to 5% ethyl acetate in petroleum ether.

NMR: δ=0.06 (m, 12H), 0.54 (s, 3H), 0.87 (s, 18H), 0.94 (m, 6H), 1.07 (d, 3H), 1.02–2.38 (m, 22H), 2.44 (dd, 1H), 2.82 (bd, 1H). 3.23 (m, 2H), 3.39 (s, 3H), 3.62 (m, 1H), 4.20 (m, 1H), 4.37 (m, 1H), 4.73 (s, 2H), 4.86 (m, 1H), 5.17 (m, 1H), 5.99 (d, 1H), 6.24 (d, 1H) ppm.

PREPARATION 38

Compound 39

Method: General Procedure 2

Starting material: Compound 25

Chromatography eluant: 2 to 5% ethyl acetate in petroleum ether.

NMR: δ=0.05 (m, 12H), 0.54 (s, 3H), 0.87 (s, 18H), 1.08 (d, 3H), 1.00–2.50 (m, 31H), 2.81 (bd, 1H), 3.25 (m, 2H), 3.48 (m, 1H), 3.69 (m, 1H), 3.95 (m, 1H), 4.18 (m, 1H), 4.37 (m, 1H), 4.85 (m, 1H), 4.98 (m, 1H), 5.17 (m, 1H), 5.99 (d, 1H), 6.23 (d, 1H) ppm.

PREPARATION 39

Compound 40

Method: General Procedure 2

Starting material: Compound 26

Chromatography eluant: 2% ether in petroleum ether.

NMR: δ=0.05 (s, 6H), 0.06 (s, 6H), 0.54 (s, 3H), 0.87 (s, 18H), 1.07 (d, 3H), 1.30 (s, 3H), 1.37 (s, 3H), 1.02–1.93 (m, 15H), 1.99 (bt, 1H), 2.13 (bd, 1H), 2.21 (dd, 1H), 2.44 (dd, 1H), 2.83 (bd, 1H), 3.22 (m, 2H), 3.56 (m, 1H), 4.19 (m, 1H), 4.37 (m, 1H), 4.86 (m, 1H), 5.17 (m, 1H), 5.99 (d, 1H), 6.24 (d, 1H) ppm.

PREPARATION 40

Compound 41

Method: General Procedure 2

Starting material: Compound 27

Chromatography eluant: 1% ether in petroleum ether.

NMR: δ=0.06 (m, 12H), 0.55 (s, 3H), 0.88 (s, 18H), 0.75–1.00 (m, 6H), 1.08 (d, 3H), 1.05–1.93 (m, 19H), 2.00 (bt, 1H), 2.16 (bd, 1H), 2.22 (dd, 1H), 2.45 (dd, 1H), 2.83 (bd, 1H), 3.18 (m, 1H), 3.25 (m, 1H), 3.60 (m, 1H), 4.20 (m, 1H), 4.38 (m, 1H), 4.87 (m, 1H), 5.18 (m, 1H), 6.01 (d, 1H), 6.25 (d, 1H).

PREPARATION 41

Compound 42

Method: General Procedure 2

Starting material: Compound 28

Chromatography eluant: 2% ethyl acetate in petroleum ether.

NMR: δ=0.05 (m, 12H), 0.53 (s, 3H), 0.87 (s, 18H), 1.07 (d, 3H), 1.32 (d, J=21.5 Hz, 6H), 1.10–1.90 (m, 17H), 1.98 (bt, 1H), 2.15 (bd, 1H), 2.20 (dd, 1H), 2.44 (dd, 1H), 2.82 (bd, 1H), 3.10–3.30 (m, 2H), 3.56 (m, 1H), 4.18 (m, 1H), 4.36 (m, 1H), 4.86 (m, 1H), 5.17 (m, 1H), 5.98 (d, 1H), 6.23 (d, 1H) ppm.

PREPARATION 42

Compound 43

Method: General Procedure 2
Starting material: Compound 29
Chromatography eluant: 2% ethyl acetate in petroleum ether.
NMR: $\delta$=0.06 (m, 12H), 0.53 (s, 3H), 0.88 (s, 18H), 0.89 (t, 6H), 1.06 (d, 3H), 1.05–2.08 (m, 22H), 2.15 (bd, 1H), 2.20 (dd, 1H), 2.44 (dd, 1H), 2.82 (m, 1H), 3.16 (m, 1H), 3.24 (m, 1H), 3.58 (m, 1H), 4.18 (m, ill), 4.36 (m, 1H), 4.86 (m, 1H), 5.17 (m, 1H), 5.99 (d, 1H), 6.24 (d, 1H) ppm.

PREPARATION 43

Compound 44

Method: General Procedure 2
Starting material: Compound 30
Chromatography eluant: 3% ether in petroleum ether.
NMR: $\delta$=0.05 (m, 12H), 0.53 (s, 3H), 0.88 (s, 18H), 1.06 (d, 3H), 1.00–1.93 (m, 17H), 1.99 (t, 1H), 2.12 (bd, 1H), 2.21 (dd, 1H), 2.44 (dd, 1H), 2.82 (bd, 1H), 3.12–3.30 (m, 2H), 3.52 (t, 2H), 3.53 (m, 1H), 4.18 (m, 1H), 4.36 (m, 1H), 4.86 (m, 1H), 5.17 (m, 1H), 5.99 (d, 1H), 6.24 (d, 1H) ppm.

PREPARATION 44

Compound 45

Method: General Procedure 2
Starting material: Compound 31
Chromatography eluant: 3% ether in petroleum ether.
NMR: $\delta$=0.05 (m, 12H), 0.53 (s, 3H), 0.87 (s, 18H), 1.06 (d, 3H), 1.05–1.93 (m, 19H), 1.98 (bt, 1H), 2.12 (bd, 1H), 2.22 (dd, 1H), 2.44 (dd, 1H), 2.82 (m, 1H), 3.12–3.30 (m, 2H), 3.52 (t, 2H), 3.48–3.60 (m, 1H), 4.18 (m, 1H), 4.37 (m, 1H), 4.86 (m, 1H), 5.17 (m, 1H), 5.99 (d, 1H), 6.24 (d, 1H) ppm.

PREPARATION 45

Compound 46

Method: General Procedure 2
Starting material: Compound 32

PREPARATION 46

Compound 47

Method: General Procedure 2
Starting material: Compound 33

PREPARATION 47

Compound 48

Method: General Procedure 2
Starting material: Compound 34

PREPARATION 48

Compound 49

Method: General Procedure 2
Starting material: Compound 35

PREPARATION 49

Compound 50

Method: General Procedure 2
Starting material: Compound 36

PREPARATION 50

Compound 51

A solution of Compound 44 (170 mg, 0.25 mmol) and tetrabutylammonium azide (285 mg, 1 mmol) in ethyl acetate (5 ml) was stirred at room temperature for 55 hours. Ethyl acetate was removed in vacuo, and the residue was extracted with ether (3×10 ml). The combined ether extracts were concentrated in vacuo and purified by chromatography (17 g silica gel, 2% ether in petroleum ether as eluant) to give the desired compound as a colourless oil.
NMR: $\delta$=0.05 (m, 12H), 0.53 (s, 3H), 0.88 (s, 18H), 1.06 (d, 3H), 1.05–1.93 (m, 17H), 1.98 (t, 1H), 2.12 (bd, 1H), 2.21 (dd, 1H), 2.44 (dd, 1H), 2.83 (bd, 1H), 3.25 (t, 2H), 3.13–3.32 (m, 2H), 3.55 (m, 1H), 4.18 (m, 1H), 4.36 (m, 1H), 4.86 (m, 1H), 5.17 (m, 1H), 5.99 (d, 1H), 6.24 (d, 1H) ppm.

PREPARATION 51

Compound 52

The compound was prepared using the method of Preparation 50, except using Compound 45 as starting material instead of Compound 44.
NMR: $\delta$=0.05 (m, 12H), 0.53 (s, 3H), 0.87 (s, 18H), 1.06 (d, 3H), 1.05–2.05 (m, 20H), 2.12 (bd, 1H), 2.21 (dd, 1H), 2.43 (dd, 1H), 2.82 (m, 1H), 3.25 (t, 2H), 3.12–3.30 (m, 2H), 3.54 (m, 1H), 4.18 (m, 1H), 4.36 (m, 1H), 4.86 (m, 1H), 5.17 (m, 1H), 5.98 (d, 1H), 6.23 (d, 1H) ppm.

GENERAL PROCEDURE 3A

Conversion of Compounds IV to the Corresponding Compounds I by Deprotection With HF The Compound IV (ca. 0.2 g) was dissolved in ethyl acetate (0.6 ml) and acetonitrile (8 ml) was added under vigorous stirring. A solution of 5% hydrofluoric acid in acetonitrile/water (8:1, 4.0 ml) was added, and the reaction mixture was stirred at room temperature for 90 minutes. Excess 4 N aqueous NaOH solution was added, and the reaction mixture was worked-up (ethyl acetate). The residue was purified by chromatography (ethyl acetate as eluant) to give the Compound I.

GENERAL PROCEDURE 3B

Conversion of Compounds IV to the Corresponding Compounds I by Deprotection with Tetra-n-butylammonium Fluoride A solution of the Compound IV (0.3 mmol) and tetra-n-butylammonium fluoride trihydrate (3.0 mmol) in THF (10 ml) was stirred at 65° C. for 1 hour. The reaction mixture was partitioned between ethyl acetate and 1% sodium hydrogen carbonate solution. Work-up and purification by chromatography (ethyl acetate as eluant) gave the title Compound I.

EXAMPLE 1

1(S), 3(R)-Dihydroxy-20(R)-(4,4-difluoro-5-hydroxy-5-methyl-hexyloxy)-9,10-seco-pregna-5(Z), 7(E), 10(19)-triene (Compound 108)

Method: General Procedure 3A

Starting material: Compound 37

NMR: δ=0.56 (s, 3H), 1.08 (d, 3H), 1.30 (bs, 1H), 1.10–2.20 (m, 20H), 2.31 (dd, 1H), 2.60 (m, 1H), 2.83 (bd, 1H), 3.25 (m, 2H), 3.63 (m, 1H), 4.23 (m, 1H), 4.43 (m, 1H), 5.00 (m, 1H), 5.32 (m, 1H), 6.00 (d, 1H), 6.38 (d, 1H) ppm.

EXAMPLE 2

1(S), 3(R)-Dihydroxy-20(R)-(5-ethyl-4,4-difluoro-5-hydroxy-heptyl-oxy)-9,10-seco-pregna-5(Z), 7(E), 10(19)-triene (Compound 109)

Method: General Procedure 3A

Starting material: Compound 38

NMR: δ=0.56 (s, 3H), 0.92 (bt, 6H), 1.08 (d, 3H), 1.05–2.20 (m, 24H), 2.31 (dd, 1H), 2.60 (dd, 1H), 2.83 (bd, 1H), 3.23 (m, 2H), 3.63 (m, 1H), 4.23 (m, 1H), 4.43 (m, 1H), 5.00 (m, 1H), 5.33 (m, 1H), 6.00 (d, 1H), 6.39 (d, 1H) ppm.

EXAMPLE 3

1(S), 3(R)-Dihydroxy-20(R)-(4,4-dichloro-5-hydroxy-5-methyl-hexyloxy)-9,10-seco-pregna-5(Z), 7(E), 10(19)-triene (Compound 129)

Method: General Procedure 3A

Starting material: Compound 39

NMR: δ=0.56 ( s, 3H), 1.09 (d, 3H), 1.50 (s, 3H), 1.52 (s, 3H), 1.00–2.50 (m, 21H), 2.60 (dd, 1H), 2.83 (m, 1H), 3.25 (m, 2H), 3.69 (m, 1H), 4.23 (m, 1H), 4.43 (m, 1H), 5.00 (m, 1H), 5.32 (m, 1H), 6.00 (d, 1H), 6.38 (d, 1H) ppm.

EXAMPLE 4

1(S), 3(R)-Dihydroxy-20(R)-(4-fluoro-4-methyl-pentyloxy)-9,10-seco-pregna-5(Z), 7(E), 10( 19)-triene (Compound 116)

Method: General Procedure 3B

Starting material: Compound 40

NMR: δ=0.56 (s, 3H), 1.08 (d, 3H), 1.31 (s, 3H), 1.38 (s, 3H), 2.32 (dd, 1H), 2.60 (dd, 1H), 1.02–2.75 (m, 19H), 2.84 (bd, 1H), 3.23 (m, 2H), 3.56 (m, 1H), 4.24 (m, 1H), 4.43 (m, 1H), 5.00 (m, 1H), 5.32 (m, 1H), 6.00 (d, 1H), 6.39 (d, 1H) ppm.

EXAMPLE 5

1(S), 3(R)-Dihydroxy-20(R)-(4-ethyl-4-fluoro-hexyloxy)-9,10-seco-pregna-5(Z), 7(E), 10(19)-triene (Compound 117)

Method: General Procedure 3B

Starting material: Compound 41

NMR: δ=0.56 (s, 3H), 0.88 (dr, 6H), 1.08 (d, 3H), 1.10–2.10 (m, 22H), 2.16 (bd, 1H), 2.31 (dd, 1H), 2.60 (dd, 1H), 2.83 (m, 1H), 3.18 (m, 1H), 3.26 (m, 1H), 3.58 (m, 1H), 4.23 (m, 1H), 4.43 (m, 1H), 5.00 (m, 1H), 5.33 (m, 1H), 6.00 (d, 1H), 6.38 (d, 1H) ppm.

EXAMPLE 6

1(S), 3(R)-Dihydroxy-20(R)-(5-fluoro-5-methyl-hexyloxyl)-9,10-seco-pregna-5(Z), 7(E), 10(19)-triene (Compound 118)

Method: General Procedure 3B

Starting material: Compound 42

NMR: δ=0.56 (s, 3H), 1.08 (d, 3H), 1.33 (d, J=21.5 Hz, 6H), 1.10–2.10 (m, 20H), 2.16 (bd, 1H), 2.31 (dd, 1H), 2.60 (m, 1H), 2.83 (m, 1H)-, 3.10–3.30 (m, 2H), 3.58 (m, 1H), 4.23 (m, 1H), 4.41 (m, 1H), 5.00 (m, 1H), 5.32 (m, 1H), 6.00 (d, 1H), 6.38 (d, 1H) ppm.

EXAMPLE 7

1(S), 3(R)-Dihydroxy-20(R)-(5-ethyl-5-fluoro-heptyloxy)-9,10-seco-pregna-5(Z), 7(E), 10(19)-triene (Compound 119)

Method: General Procedure 3B

Starting material: Compound 43

NMR: δ=0.56 (s, 3H), 0.88 (m, 6H), 1.08 (d, 3H), 1.10–2.10 (m, 24H), 2.16 (bd, 1H), 2.31 (dd, 1H), 2.60 (dd, 1H), 2.83 (m, 1H), 3.17 (m, 1H), 3.24 (m, 1H), 3.58 (m, 1H), 4.22 (m, 1H), 4.42 (m, 1H), 5.00 (m, 1H), 5.33 (m, 1H), 6.00 (d, 1H), 6.39 (d, 1H) ppm.

EXAMPLE 8

1(S), 3(R)-Dihydroxy-20(R)-(5-azido-pentyloxy)-9,10-seco-pregna-5(Z), 7(E), 10(19)-triene (Compound 134)

Method: General Procedure 3B

Starting material: Compound 44

NMR: δ=0.55 (s, 3H), 1.07 (d, 3H), 1.05–2.07 (m, 20H), 2.13 (bd, 1H), 2.32 (dd, 1H), 2.60 (dd, 1H), 2.84 (bd, 1H), 3.26 (t, 2H), 3.13–3.32 (m, 2H), 3.56 (m, 1H), 4.23 (m, 1H), 4.43 (m, 1H), 5.00 (m, 1H), 5.32 (m, 1H), 6.00 (d, 1H) ppm.

EXAMPLE 9

1(S), 3(R)-Dihydroxy-20(R)-(6-azido-hexyloxy)-9,10-seco-pregna-5(Z), 7(E), 10(19)-triene (Compound 135)

Method: General Procedure 3B

Starting material: Compound 45

NMR: δ=0.55 (s, 3H), 1.07 (d, 3H), 1.05–2.10 (m, 22H), 2.14 (bd, 1H), 2.31 (dd, 1H), 2.60 (dd, 1H), 2.84 (m, 1H), 3.26 (t, 2H), 3.12–3.30 (m, 2H), 3.55 (m, 1H), 4.23 (m, 1H), 4.43 (m, 1H), 5.00 (m, 1H), 5.32 (m, 1H), 6.00 (d, 1H), 6.39 (d, 1H) ppm.

EXAMPLE 10

Capsules containing Compound 109

Compound 109 was dissolved in arachis oil to a final concentration of 1 µg of Compound 109/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 µl of Compound 109 in oil solution, such that each capsule contained 0.1 µg of Compound 109.

EXAMPLE 11

Dermatological Cream Containing Compound 109

In 1 g almond oil was dissolved 0.05 mg of Compound 109. To this solution was added 40 g of mineral oil and 20 g of self-emulsifying beeswax. The mixture was heated to liquify. After the addition of 40 ml hot water, the mixture was mixed well. The resulting cream contains approximately 0.5 µg of Compound 109 per gram of cream.

What we claim is:

1. A compound of formula I

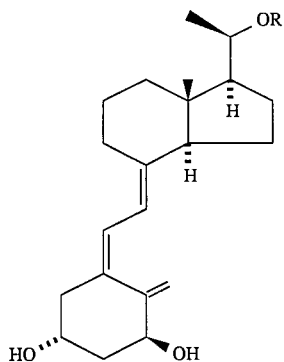

in which R stands for a straight or branched, saturated or unsaturated alkyl group containing from 4 to 12 carbon atoms optionally substituted with a hydroxy group, and possibly containing a ring structure, and in which at least one of the carbon atoms not bearing a hydroxyl group is substituted with one or more halogen atoms or an azido group; and prodrugs of I in which one or more of the hydroxy groups are masked as groups which can be reconverted to hydroxy groups in vivo.

2. A compound according to claim 1 in which R is a group of formula II

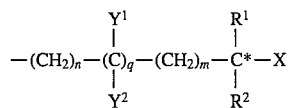

where q is 0 or 1, and n and m are independently 0 or integers running from 1 to 6; $Y^1$ and $Y^2$ are independently hydrogen, halogen or azido; $R^1$ and $R^2$, which may be the same or different, stand for hydrogen, lower alkyl, lower cycloalkyl, or, taken together with the carbon atom (starred in formula II) bearing the group X, $R^1$ and $R^2$ can form a $C_3$-$C_8$ carbocyclic ring; $R^1$ and $R^2$ may optionally be substituted with an azido group or one or more halogen atoms; X stands for hydrogen or hydroxy, the sum of n+q+m is at least 2 and at least one of $Y^1$, $Y^2$, $R^1$ and $R^2$ is halogen or azido provided that when q is 0, at least one of $R^1$ and $R^2$ is halogen or azido.

3. A compound according to claim 2 in which q is 1, m is 0 and n is an integer from 2–4; $Y^1$ and/or $Y^2$ stand for fluorine.

4. A compound according to claim 1 which is

1(S), 3(R)-Dihydroxy-20(R)-(5-ethyl-4,4-difluoro-5-hydroxy-heptyloxy)-9,10-seco-pregna-5(Z), 7(E), 10(19)-triene, 1(S), 3(R)-Dihydroxy-20(R)-(4,4-dichloro-5-hydroxy-5-methyl-hexyloxy)-9,10-seco-pregna-5(Z), 7(E), 10(19)-triene, 1(S), 3(R)-Dihydroxy-20(R)-(4,4-difluoro-5-hydroxy-5-methyl-hexyloxy)-9,10-seco-pregna-5(Z), 7(E), 10(19)-triene, 1(S), 3(R)-Dihydroxy-20(R)-(4-fluoro-4-methyl-pentyloxy)-9,10-seco-pregna-5(Z), 7(E), 10(19)-triene, 1(S), 3(R)-Dihydroxy-20(R)-(4-ethyl-4-fluoro-hexyloxy)-9,10-seco-pregna-5(Z), 7(E), 10(19)-triene, 1(S), 3(R)-Dihydroxy-20(R)-(5-fluoro-5-methyl-hexyloxy)-9,10-seco-pregna-5(Z), 7(E), 10(19)-triene, 1(S), 3(R)-Dihydroxy-20(R)-(5-ethyl-5-fluoro-heptyloxy)-9,10-seco-pregna-5(Z), 7(E), 10(19)-triene, 1(S), 3(R)-Dihydroxy-20(R)-(5-azido-pentyloxy)-9,10-seco-pregna-5(Z), 7(E), 10(19)-triene or 1(S), 3(R)-Dihydroxy-20(R)-(6-azido-hexyloxy)-9,10-seco-pregna-5(Z), 7(E), 10(19)-triene.

5. A pharmaceutical composition containing an effective amount of one or more of the compounds of claim 1, together with a pharmaceutically acceptable, non-toxic carrier.

6. A pharmaceutical composition according to claim 5 in dosage unit form containing from 0.1 ppm to 0.1% by weight of the dosage unit of a compound of formula I.

7. A method for the treatment of a disease state selected from the group consisting of hyperparathyroidism, hypertension, acne, imbalance in the immune system, rheumatoid arthritis, asthma, abnormal cell differentiation; abnormal cell proliferation and steroid induced skin atrophy, which comprises administering to a patient in need thereof an effective amount of a pharmaceutical composition according to claim 5.

8. A method for the promotion of osteogenesis and the treatment of osteoporosis which comprises administering to a patient in need thereof, an effective amount of a composition according to claim 5.

* * * * *